United States Patent [19]

Martin et al.

[11] 4,124,756

[45] Nov. 7, 1978

[54] 3-DE-O-METHYLFORTIMICINS

[75] Inventors: Jerry R. Martin; John S. Tadanier, both of Waukegan, Ill.

[73] Assignee: Abbott Laboratories, North Chicago, Ill.

[21] Appl. No.: 754,670

[22] Filed: Dec. 27, 1976

[51] Int. Cl.$^2$ .................................... C07H 15/22
[52] U.S. Cl. ............................ 536/17; 424/180; 424/181; 536/4
[58] Field of Search ............................ 536/17, 4

[56] References Cited

U.S. PATENT DOCUMENTS

| | | | |
|---|---|---|---|
| 3,350,387 | 10/1967 | Vanderhaeghe | 536/17 |
| 3,792,037 | 2/1974 | Kawaguchi et al. | 536/17 |
| 3,925,353 | 12/1975 | Umezawa et al. | 536/17 |
| 3,985,727 | 10/1976 | Daniels | 536/17 |

Primary Examiner—Johnnie R. Brown
Attorney, Agent, or Firm—Robert L. Niblack; Gildo E. Fato

[57] ABSTRACT

Described are 3-de-O-methylfortimicins A and B and 4-N-acyl and 4-N-alkyl-3-de-O-methylfortimicin B derivatives, and their preparation, which compounds are useful as antibiotics or as intermediates for preparing other useful derivatives having antibacterial activity. The compounds have the following structural formula

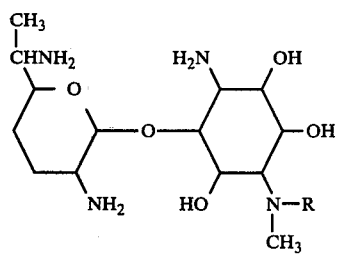

wherein R is hydrogen, acyl, aminoacyl, N-monoloweralkylaminoacyl, N,N-diloweralkylaminoacyl, hydroxy-substituted aminoacyl, alkyl, aminoalkyl, N-monoloweralkylaminoalkyl, N,N-diloweralkylaminoalkyl or hydroxy-substituted aminoalkyl and the pharmaceutically acceptable salts thereof, for example, salts formed from hydrochloric, sulfuric, and phosphoric acids.

8 Claims, No Drawings

3-DE-O-METHYLFORTIMICINS

DETAILED DESCRIPTION OF THE INVENTION

The present invention relates to the preparation of 3-de-O-methylfortimicins A and B and 4-N-acyl- and 4-N-alkyl 3-de-O-methylfortimicin B derivatives which are useful as antibiotics or as intermediates for preparing other useful derivatives having antibacterial activity. The novel compounds of this invention have the following structural formula

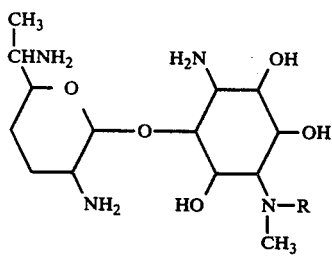

wherein R is hydrogen, acyl, aminoacyl, N-monoloweralkylaminoacyl, N,N-diloweralkylaminoacyl, hydroxy-substituted aminoacyl, alkyl, aminoalkyl, N-monoloweralkylaminoalkyl, N,N-diloweralkylaminoalkyl or hydroxy-substituted aminoalkyl and the pharmaceutically acceptable salts thereof, for example, salts formed from hydrochloric, sulfuric, and phosphoric acids.

The naturally occurring fortimicins are produced in several forms by cultivation of a strain of *Micromonospora olivoasterospora* in a suitable nutrient medium as taught in U.S. Pat. No. 3,931,400 issued Jan. 6, 1976 and U.S. Pat. No. 3,976,768, issued Aug. 24, 1976. The structure of two of these forms is represented by the following formula

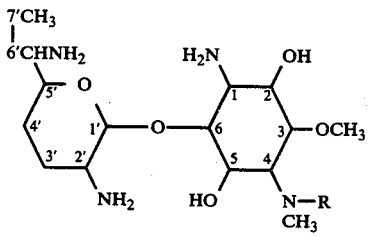

In this formula, when R is hydrogen the structure illustrated is fortimicin B. When R is glycyl the structure of fortimicin A is shown. As denoted in the formula above, the fortimicin compounds consist of two cyclic moieties referred to respectively as purpurosamine and fortamine. The positions of the purpurosamine ring are indicated by primed numbers while the positions on the aminocyclitol moiety, fortamine, are indicated by unprimed numbers.

According to the method of this invention, in performing the 3-O-demethylation reaction, fortimicin B, or other appropriate derivative containing the fortamine moiety are reacted with excess metalic lithium in an amine solvent such as ethylamine or ethylenediamine. The reactants are admixed in the solvent and the reaction allowed to proceed at a suitable temperature for the desired period. The resulting 3-de-O-methylfortimicin β, 4-N-(B-aminoethyl)-3-de-O-methylfortimicin B, or other derivative is isolated by conventional column chromatographic methods.

The 3-de-O-methylfortimicin B prepared above is reacted with N-(benzyloxycarbonyloxy)-succinimide to prepare 1, 2', 6'-tri-N-benzyloxycarbonyl-3-de-O-methylfortimicin B by following the procedures outlined in U.S. patent application Ser. No. 725,820 filed Sept. 23, 1976, now abandoned. The product formed in the above reaction is isolated by column chromatography and 4-N-acylated by treatment with suitable N-benzyloxycarbonyl protected amino acids suitably activated as taught in U.S. patent application Ser. No. 725,820 filed Sept. 23, 1976. The benzyloxycarbonyl-3-de-O-methyl-4-N-acyl fortimicins prepared as above are conveniently reduced to the corresponding 4-N-alkyl derivatives with diborane. After isolation by column chromatography the benzyloxycarbonyl groups of both the 4-N-acyl and 4-N-alkyl derivatives are conveniently removed by catalylic hydrogenolysis and the products may be isolated as the hydrochloride salts as outlined in U.S. patent application Ser. No. 725,820 filed Sept. 23, 1976.

The following examples more clearly illustrate the invention but are not intended to limit the scope of the invention to the examples described.

EXAMPLE 1

3-De-O-methylfortimicin B

To a solution of 2.0 g of fortimicin B free base in 50 ml. of freshly distilled ethylamine is added 40 ml. of ethylamine containing 0.859 g. of lithium wire freshly cut into small pieces. The dark blue reaction mixture is stirred under reflux for 2 hours, then methanol is slowly added to consume excess lithium. The solvents are removed under reduced pressure and the resulting organic products are separated from the lithium salts by column chromatography on silica gel prepared and eluted with the lower phase of a mixture of chloroform-methanol-concentrated ammonium hydroxide (1:1:1 v/v/v). Fractions enriched in 3-de-O-methylfortimicin B are collected and rechromatographed on a column of a cation exchange resin, acrylic type, such as Bio Rex 70, 100–200 mesh, $NH_4$ form. Elution with a gradient of water to 1N $NH_4OH$ gave fractions containing pure 3-de-O-methylfortimicin B. Lyophilization gave 0.267 g of colorless material: $[\alpha]_D^{24}$ +41.4° (c 1.02, $CH_3OH$); IR 3370, 1585 cm$^{-1}$; PMR ($D_2O$) δ 1.5 ($C_6'$-$CH_3$, $J_{6',7'}$ = 6.5), 2.83 ($C_4$—N—$CH_3$), 5.53 ($H_{1'}$, $J_{1',2}$ = 3.8); Mass spec M + 334.222 Calculated for $C_{14}H_{30}N_4O_5$ 334.2216.

EXAMPLE 2

1, 2', 6'-Tri-N-benzyloxycarbonyl-3-de-O-methylfortimicin B

To a stirring, ice-bath cooled solution of 3-de-O-methylfortimicin B free base (1.59 g) in 24 ml. water and 48 ml. methanol is added 3.55 g of N-(benzyloxycarbonyloxy)-succinimide. The reaction is stirred at ice-bath temperature for 4 hours and then at room temperature for 22 hours. The reaction is concentrated under reduced pressure and poured into 400 ml. water to which is added 200 ml. chloroform. The organic layer is separated and washed with water and dried ($MgSO_4$). The chloroform is evaporated and the residue chromatographed on silica gel prepared and eluted with a solvent system consisting of chloroform-methanol-concentrated ammonium hydroxide (23.4:1.4:0.1 v/v/v). Fractions containing pure 1, 2', 6'-tri-N-benzyloxycarbonyl-3-de-O-methylfortimicin B are collected and evaporated to dryness to give 1.70 g of product: $[\alpha]_D^{23}$ + 19.4° (c 1.0, CH$_3$OH); IR 3437, 3350, 1705, 1505 cm$^{-1}$; PMR (CDCl$_3$) δ 0.99 (C$_6$'-CH$_3$, J$_{6',7'}$ = 5.0), 2.27 (C$_4$—N—CH$_3$), 7.27 (Cbz).

Analysis: Calculated for C$_{33}$H$_{48}$N$_4$O$_{11}$: C, 61.94; H, 6.57; N, 7.60; Found: C, 61.83; H, 6.74; N, 7.51.

EXAMPLE 3

Tetra-N-benzyloxycarbonyl-3-de-O-methylfortimicin A

To a stirred solution of 0.80 g of 1, 2', 6'-tri-N-benzyloxycarbonyl-3-de-O-methylfortimicin B in 5.35 ml of tetrahydrofuran is added 0.399 g of N-hydroxysuccinimidyl-N-benzyloxycarbonylglycine. Stirring is continued for 22 hours at room temperature. The reaction is concentrated to dryness under reduced pressure and the resulting product chromatographed on a column of silica gel with a solvent system consisting of benzene-methanol-95% ethanol-concentrated ammonium hydroxide (23.5:1.4:2.0:0.2 v/v/v/v). Fractions containing the desired product are taken to dryness to give 0.488 g of tetra-N-benzyloxycarbonyl-3-de-O-methylfortimicin A as a colorless glass: $[\alpha]_D^{24}$ + 45.2° (c 1.03, CH$_3$OH); IR 3425, 1705, 1645, 1500 cm$^{-1}$; PMR (CDCl$_3$) δ 1.15 (C$_6$'—CH$_3$), 2.9 (C$_4$—N—CH$_3$), 7.28 (Cbz).

Analysis: Calculated for C$_{48}$H$_{57}$N$_5$O$_{14}$: C, 62.13; H, 6.19; N, 7.55; Found: C, 61.80; H, 6.31; N, 7.64.

EXAMPLE 4

Tetra-N-benzyloxycarbonyl-3-de-O-methylfortimicin A

To a stirred solution of 0.525 g of 1, 2', 6'-tri-N-benzyloxycarbonyl-3-de-O-methylfortimicin B, 0.199 g of N-benzyloxycarbonylglycine and 0.228 g of 1-hydroxybenzotriazole monohydrate in 3.0 ml tetrahydrofuran is added 0.88 g of N,N'-dicyclohexylcarbodiimide dissolved in 1.5 ml tetrahydrofuran. An additional 1.5 ml of tetrahydrofuran is used to rinse all the N,N'-dicyclohexylcarbodiimide into the reaction vessel. Stirring is continued for 22 hours at ambient temperature. Insoluble dicyclohexylurea is removed by filtration. The filtrate is concentrated to dryness under reduced pressure to yield a yellow froth. The froth is chromatographed on a column of silica gel using a solvent system consisting of benzene-methanol-95% ethanol-concentrated ammonium hydroxide (23.5:1.4:2.0:0.2 v/v/v/v). Fractions containing the majority of the product are taken to dryness and rechromatographed on a column of Sephadex LH20 prepared and eluted with 95% ethanol. Fractions containing pure product are collected and the solvent removed under reduced pressure to give 0.105 g of tetra-N-benzyloxycarbonyl-3-de-O-methylfortimicin A identical in all respects with the same material prepared in Example 3.

EXAMPLE 5

Tetra-N-benzyloxycarbonyl-3-de-O-methyl-4-N-sarcosylfortimicin B

To a stirred solution of 0.298 g of 1, 2', 6'-tri-N-benzyloxycarbonyl-3-de-O-methylfortimicin B, 0.113 g of N-benzyloxycarbonylsarcosine and 0.129 g of 1-hydroxybenzotriazole in 3.0 ml of tetrahydrofuran is added 0.107 g of N,N'-dicyclohexylcarbodiimide in 1.5 ml tetrahydrofuran. An additional 1.5 ml of tetrahydrofuran is used to rinse all the N,N'-dicyclohexylcarbodiimide into the reaction flask. Stirring is continued for 16 hours at room temperature. Insoluble dicyclohexylurea is removed by filtration and the filtrate concentrated to yield a pale yellow solid. The solid is chromatographed on a column of silica gel using a solvent system consisting of benzene-methanol-95% ethanol-concentrated ammonium hydroxide (23.5;1.4;2.0;0.2 v/v/v). Fractions containing homogeneous material are taken to dryness. Other fractions containing a minor second component are rechromatographed on a column of silica gel using a solvent system consisting of benzene-methanol-concentrated ammonium hydroxide (85:15:1 v/v/v). Homogeneous fractions are combined with material obtained in the first column to give 0.709 g of tetra-N-benzyloxycarbonyl-3-de-0-methyl-4-N-sarcosylfortimicin B as a glass: $[\alpha]_D^{24}$ + 42.9° (c 1.01, CH$_3$OH); IR 3435, 1703, 1635, 1500 cm$^{-1}$; PMR (CDCl$_3$) δ 1.17 (C$_6$'—CH$_3$), ~ 2.9 (broad) (Sarcosyl-N-CH$_3$), 2.99 (C$_4$—N—CH$_3$), 4.83 (H$_{1'}$, J$_{1',2'}$ = 3.5), 7.31 (Cbz).

Analysis: Calculated for C$_{49}$H$_{59}$N$_5$O$_{14}$: C, 62.48; H, 6.31; N, 7.43; Found: C, 62.35; H, 6.65; N, 7.57.

EXAMPLE 6

3-De-O-methylfortimicin A tetrahydrochloride

Tetra-N-benzyloxycarbonyl-3-de-O-methylfortimicin A (0.14 g) in 25 ml 0.2 N hydrochloric acid in methanol is hydrogenolyzed for 4 hours under 3 atmospheres of hydrogen in the presence of 0.1 g of 5% palladium on carbon. The catalyst is removed by filtration and the filtrate concentrated to dryness under reduced pressure. Excess acid is removed by co-distillation with methanol under reduced pressure to give 0.071 g of 3-de-O-methylfortimicin A tetrahydrochloride: $[\alpha]_D^{23}$ + 79.4° (c 1.0, CH$_3$OH); IR 3410, 2930, 1639, 1595, 1483 cm$^{-1}$; PMR (D$_2$O) δ 1.81 (C$_6$'—CH$_3$, J$_{6'7}$ = 6.5), 3.62 (C$_4$—N—CH$_3$), 5.79 (H$_{1'}$, J$_{1',2'}$ = 3.5); Mass spec. M + 391.2414, Calculated for C$_{16}$H$_{33}$N$_5$O$_6$ 391.2431.

EXAMPLE 7

3-De-O-methyl-4-N-sarcosylfortimicin B tetrahydrochloride

Tetra-N-benzyloxycarbonyl-3-de-O-methyl-4-N-sarcosylfortimicin B(0.125 g) in 25 ml 0.2 N hydrochloric acid in methanol is hydrogenolyzed for 4 hours under 3 atmospheres of hydrogen in the presence of 0.13 g of 5% palladium on carbon. The catalyst is removed by filtration and the filtrate concentrate to dryness under reduced pressure. Excess acid is removed by co-distillation with methanol under reduced pressure to give 0.073 g of 3-de-O-methyl-4-N-sarcosylfortimicin B tetrahydrochloride: $[\alpha]_D^{24}$ + 83.5° (c 1.01, CH$_3$OH); IR 3420, 2930, 1635, 1485 cm$^{-1}$; PMR (D$_2$O) 1.8 (C$_6$'—CH$_3$, J$_{6',7}$ = 6.5), 3.27 (Sarcosyl—N—CH$_3$), 3.6 (C$_4$—N—CH$_3$), 5.79 (H$_{1'}$, J$_{1',2'}$ = 3.5); Mass Spec M + 405.2614, Calculated for C$_{17}$H$_{35}$N$_5$O$_6$ 405.2587.

EXAMPLE 8

Tetra-N-benzyloxycarbonyl-3-de-O-methyl-4-N-(B-aminoethyl) fortimicin B

To an ice cold stirred solution of 0.3 g of tetra-N-benzyloxycarbonyl-3-de-O-methylfortimicin A dry tetrahydrofuran (6 ml.) is added 1.0 ml of a 1 M solution of diborane in tetrahydrofuran. The reaction mixture is stirred for 3 hours under a nitrogen atmosphere and then treated with an additional 1.0 ml. of the diborane solution. After stirring for an additional 2 hours under nitrogen water is added and the solvents evaporated under reduced pressure. Purification by column chromatography on silica gel prepared and eluted with a solvent system consisting of chloroform-methanol-concentrated ammonium hydroxide (23.4:1.4:0.1 v/v/v) gave pure tetra-N-benzyloxycarbonyl-3-de-O-methyl-4-N-(B-aminoethyl) fortimicin B.

EXAMPLE 9

3-de-O-methyl-4-N-(B-aminoethyl)fortimicin B tetrahydrochloride

Tetra-N-benzyloxycarbonyl-3-de-O-methyl-4-N-(B-aminoethyl) fortimicin B (0.10 g) in 25 ml. 0.2 N hydrochloric acid in methanol is hydrogenolyzed for 4 hours under 3 atmospheres of hydrogen in the presence of 0.11 g of 5% pallidium on carbon. The catalyst is removed by filtration and the filtrate concentrated to dryness under reduced pressure. Excess acid is removed by co-evaporation with methanol under reduced pressure to give 3-de-O-methyl-4-N-(B-aminoethyl) fortimicin B tetrahydrochloride.

EXAMPLE 10

3-De-O-methyl-4-N-(B-aminoethyl) fortimicin B

To a solution of 1.0 g of 4-N-(B-aminoethyl)fortimicin B in 25 ml of freshly distilled ethylamine is added 20 ml. of ethylamine containing 0.430 g of lithium wire freshly cut into small pieces. The dark blue reaction mixture is stirred under reflux for 2-16 hours, then methanol is cautiously added to consume the excess lithium. The solvent is evaporated under reduced pressure and the residue chromatographed on silica gel prepared and eluted with the lower phase of a mixture of chloroform-methanol-concentrated ammonium hydroxide (1:1:1 v/v/v). Fractions containing the desired product are collected and rechromatographed on a column of a weakly acidic, carboxylic (polymethacrylic) type, cation exchange resin in the ammonia form, for example, Biorex 70, 100-200 mesh. Elution with a gradient of water to 1 N NH4OH gave fractions containing pure 3-de-O-methyl-4-N-(B-aminoethyl)fortimicin B.

EXAMPLES 11-13

In Vitro Antibiotic Activities of 3-De-O-methylfortimicins B and A and 3-De-O-methyl-4-N-sarcosylfortimicin B The in vitro antibiotic acitivites of the following 3-de-O-methylfortimicins
(11) 3-De-O-methylfortimicin B
(12) 3-De-O-methylfortimicin A tetrahydrochloride
(13) 3-De-O-methyl-4-N-sarcosylfortimicin B tetrahydrochloride
are listed in Table 1.

The in vitro antibiotic activities were determined by a two-fold agar dilution method using Mueller-Hinton agar, 10 ml per Petri plate. The agar was inoculated with one loopful (0.001 ml loop) of a 1:10 dilution of a 24 hour broth culture of the indicated test organism and incubated at 37° C. for 24 hours. Appropriate fortimicins were used as control antibiotics. The activities are listed in Table 1. Minimum inhibitory concentrations (MIC) are expressed as mcg/ml.)

TABLE 1

In Vitro Antibiotic Activity of 3-De-O-Methylfortimicins

| Organism | Fortimicin A Tetrahydrochloride | Fortimicin B (free base) | Compound 11 | 12 | 13 |
|---|---|---|---|---|---|
| *Staphylococcus aureus* Smith | 1.56 | >100 | >100 | 0.54 | 1.56 |
| *Streptococcus faecalis* 10541 | 100 | >100 | >100 | 17 | 100 |
| *Enterobacter aerogenes* 13048 | 3.1 | >100 | >100 | 2.1 | 3.1 |
| *Escherichia coli* Juhl | 12.5 | >100 | >100 | 2.1 | 12.5 |
| *Escherichia coli* BL 3676 (Resist) | 25 | >100 | >100 | 8.6 | 25 |
| *Klebsiella pneumoniae* 10031 | 3.1 | >100 | >100 | 1.1 | 3.1 |
| *Klebsiella pneumoniae* KY 4262 | 6.2 | >100 | >100 | 8.6 | 6.2 |
| *Providencia* 1577 | 3.1 | >100 | >100 | 1.1 | 3.1 |
| *Pseudomonas aeruginosa* BMH #10 | 0.78 | >100 | >100 | 0.27 | 0.78 |
| *Pseudomonas aeruginosa* KY 8512 | 12.5 | >100 | >100 | 2.1 | 12.5 |
| *Pseudomas aeruginosa* KY 8516 | 50 | >100 | >100 | 69 | 25 |
| *Pseudomonas aeruginosa* 209 | >100 | >100 | >100 | >69 | >100 |
| *Salmonella typhimurium* ED #9 | 3.1 | >100 | >100 | 1.1 | 3.1 |
| *Serratia marcesceus* 4003 | 3.1 | >100 | >100 | 4.3 | 3.1 |
| *Shigella sonnei* 9290 | 12.5 | >100 | >100 | 4.3 | 6.2 |
| *Proteus rettgeri* U 6333 | 50 | >100 | >100 | 17 | 50 |
| *Proteus vulgaris* Abbott JJ | 6.2 | >100 | >100 | 2.1 | 6.2 |
| *Proteus mirabilis* Fin. #9 | 6.2 | >100 | >100 | 2.1 | 6.2 |

What is claimed is:

1. A compound of the formula

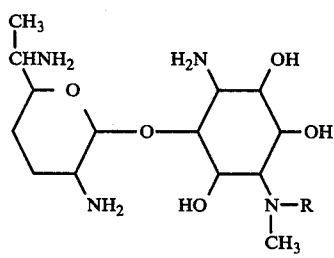

wherein R is a member of the group consisting of hydrogen, lower acyl, lower amino acyl, N-monoloweralkyl loweraminoacyl, N,N-di-loweralkyl loweraminoacyl, hydroxy-substituted loweraminoacyl, loweralkyl, loweraminoalkyl, N-monoloweralkyl loweraminoalkyl, N,N-diloweralkyl loweraminoalkyl, or hydroxysubstituted loweraminoalkyl and the pharmaceutically acceptable salts thereof.

2. A compound selected from the group consisting of 3-De-O-methylfortimicin B, 1, 2', 6'-Tri-N-benzyloxycarbonyl-3-de-O-methylfortimicin B, Tetra-N-benzyloxycarbonyl-3-de-O-methylfortimicin A, Tetra-N-benzyloxycarbonyl-3-de-O-methylfortimicin A, Tetra- N-benzyloxycarbonyl-3-de-O-methyl-4-N-sarcasylfortimicin B, 3-De-O-methylfortimicin A tetrahydrochloride, 3-De-O-methyl-4-N-sarcosylfortimicin B tetrahydrochloride, Tetra-N-benzyloxycarbonyl-3-de-O-methyl-4-N-(β-aminoethyl) fortimicin B, 3-de-O-methyl-4-N-(β-aminoethyl)fortimicin B tetrahydrochloride, 3-de-O-methyl-4-N-(β-aminoethyl) fortimicin B, 3-De-O-methylfortimicin B, 3-De-O-methylfortimicin A tetrahydrochloride, 3-De-O-methyl-4-N-sarcosylfortimicin B tetrahydrochloride.

3. A compound selected from the group consisting of 3-de-O-metylfortimicin B, 3-de-O-methylfortimicin A tetrahydrochloride, 3-de- O-metyl-4-N-sarcosylfortimicin B tetrahydrochloride, 3-de-O-methyl-4-N-(β-aminoethyl)fortimicin B tetrahydrochloride, 3-de-O-methyl-4-N-(β-aminoethyl) fortimicin B.

4. A compound selected from the group consisting of 3-de-O-methylfortimicin B, 3-de-O-methylfortimicin A tetrahydrochloride, 3-de-O-methyl-4-N-sarcosylfortimicin B tetrahydrochloride.

5. The compound of claim 4: 3-de-O-methylfortimicin B.

6. The compound of claim 4: 3-de-O-methylfortimicin A tetrahydrochloride.

7. The compound of claim 4: 3-de-O-methyl-4-N-sarcosylfortimicin B tetrahydrochloride.

8. A method of preparing 3-de-O-methyl-4-N-acyl fortimicins comprising:
reacting 3-de-O-methylfortimicin B with N-(benzyloxycarbonyloxy)succinimide to form the 1, 2', 6'-tri-N-benzyloxycarbonyl protected 3-de-O-methylfortimicins,
reacting of said protected 3-de-O-methylfortimicins with suitable activated N-benzyloxycarbonyl protected amino acids to form the benzyloxycarbonyl-3-de-O-methyl-4-N-acylfortimicin, and
removing the N-benzyloxycarbonyl groups by hydrogenolysis with a suitable catalyst in the presence of an acid to form the desired 3-de-O-methyl-4-N-acylfortimicin acid salts.

* * * * *

UNITED STATES PATENT OFFICE
CERTIFICATE OF CORRECTION

PATENT NO. : 4,124,756
DATED : November 7, 1978
INVENTOR(S) : John Soloman Tadanier and Jerry Roy Martin It is certified that error appears in the above-identified patent and that said Letters Patent are hereby corrected as shown below:

Col. 2, line 7 "725,820" should be -- 725,829 --;

Col. 2, line 8, after "1976" delete ", now abandoned";

Col. 2, line 13 "725,820" should be -- 725,829 --;

Col. 2, line 21 "725,820" should be -- 725,829 --.

Signed and Sealed this

Twenty-fifth Day of March 1980

[SEAL]

Attest:

SIDNEY A. DIAMOND

Attesting Officer     Commissioner of Patents and Trademarks